(12) United States Patent
Susko

(10) Patent No.: US 9,298,193 B2
(45) Date of Patent: *Mar. 29, 2016

(54) OPTICAL PROBE CONTAINING OXYGEN, TEMPERATURE, AND PRESSURE SENSORS AND MONITORING AND CONTROL SYSTEMS CONTAINING THE SAME

(71) Applicant: Patricia Susko, Elmont, NY (US)

(72) Inventor: Kenneth Susko, Elmont, NY (US)

(73) Assignee: Kenneth Susko, Elmont, NY (US)

( * ) Notice: Subject to any disclaimer, the term of this patent is extended or adjusted under 35 U.S.C. 154(b) by 35 days.

This patent is subject to a terminal disclaimer.

(21) Appl. No.: 13/837,286

(22) Filed: Mar. 15, 2013

(65) Prior Publication Data

US 2013/0206760 A1 Aug. 15, 2013

Related U.S. Application Data

(63) Continuation-in-part of application No. 13/279,994, filed on Oct. 24, 2011.

(60) Provisional application No. 61/406,050, filed on Oct. 22, 2010.

(51) Int. Cl.
  *G05D 11/13* (2006.01)
  *B64D 37/32* (2006.01)
  (Continued)

(52) U.S. Cl.
  CPC .............. *G05D 11/131* (2013.01); *B64D 37/32* (2013.01); *G01D 11/245* (2013.01);
  (Continued)

(58) Field of Classification Search
  CPC .......... G01K 11/3206; G01K 11/3213; G01D 11/245
  USPC ...................................... 137/487.5
  See application file for complete search history.

(56) References Cited

U.S. PATENT DOCUMENTS 4,378,920 A * 4/1983 Runnels et al. ............ 244/135 R
4,556,180 A * 12/1985 Manatt ....................... 244/135 R (Continued)

FOREIGN PATENT DOCUMENTS

DE         4018998 A1    1/1992
DE     202006016081 U1   2/2007
(Continued)

OTHER PUBLICATIONS

Panahi A: "Fiber optic oxygen sensor using fluorescence quenching for aircraft inerting fuel tank applications", proceedings of SPIE, International Society for Optical Engineering, US, vol. 7314, May 20, 2009, pp. 73140D-1, XP002633834, ISSN: 0277-786X, DOI: 10.1117/12.821732, ISBN: 978-0-8194-9923-3.

(Continued)

*Primary Examiner* — Craig Schneider
*Assistant Examiner* — Kevin Barss
(74) *Attorney, Agent, or Firm* — Dickinson Wright PLLC

(57) ABSTRACT

A probe for measuring oxygen, temperature, and pressure in a space to be monitored, comprising: a housing, comprising a thermally conductive material; an oxygen sensor disposed within the housing, comprising: a first end having coated thereon a coating which fluoresces at a fluorescent frequency when exposed to light having an excitation frequency in the absence of associated oxygen, and which undergoes a dampening of said fluorescence in the presence of associated oxygen; and a second end operatively connected to an optical fiber that extends through the housing; wherein the first end extends through the housing and is adapted to be exposed to the space to be monitored; a temperature sensor disposed within the housing adjacent to the thermally conductive material, comprising a fiber Bragg grating, or a semiconductor material, such as a GaAS material, wherein the temperature sensor does not extend through the housing and is not exposed to the space to be monitored; a pressure sensor disposed within the housing, comprising a fiber Bragg grating or a Fabry-Pérot white light interferometry sensor having a first end which extends through the housing and is adapted to be exposed to the space to be monitored.

12 Claims, 4 Drawing Sheets

(51) Int. Cl.
*G01K 13/00* (2006.01)
*G01D 11/24* (2006.01)
*G01K 11/32* (2006.01)
*G01N 21/77* (2006.01)
*G01N 21/64* (2006.01)
*G01L 7/02* (2006.01)
*G01D 5/26* (2006.01)

(52) U.S. Cl.
CPC ........... *G01K 11/3206* (2013.01); *G01K 13/00* (2013.01); *G01L 7/026* (2013.01); *G01N 21/643* (2013.01); *G01N 21/7703* (2013.01); *G01D 5/266* (2013.01); *G01D 5/268* (2013.01); *G01N 2021/6432* (2013.01); *G01N 2021/772* (2013.01); *G01N 2021/7786* (2013.01); *Y10T 137/034* (2015.04); *Y10T 137/2509* (2015.04)

(56) References Cited

U.S. PATENT DOCUMENTS

| | | | | |
|---|---|---|---|---|
| 4,749,254 | A * | 6/1988 | Seaver | 385/12 |
| 4,822,135 | A * | 4/1989 | Seaver | 385/13 |
| 6,634,598 | B2 * | 10/2003 | Susko | 244/135 R |
| 6,739,399 | B2 * | 5/2004 | Wagner et al. | 169/45 |
| 6,904,930 | B2 * | 6/2005 | Susko | 137/209 |
| 6,925,852 | B2 * | 8/2005 | Susko | 73/23.2 |
| 7,181,096 | B2 * | 2/2007 | Matsumoto et al. | 385/12 |
| 7,191,983 | B2 * | 3/2007 | Loss et al. | 244/135 R |
| 7,289,836 | B2 * | 10/2007 | Colvin, Jr. | 600/316 |
| 7,352,464 | B2 * | 4/2008 | Chen et al. | 356/437 |
| 7,431,695 | B1 * | 10/2008 | Creaghan | 600/249 |
| 7,433,551 | B2 * | 10/2008 | Poland et al. | 385/12 |
| 7,481,237 | B2 * | 1/2009 | Jones et al. | 137/12 |
| 7,509,968 | B2 * | 3/2009 | Surawski | 137/209 |
| 7,568,395 | B2 * | 8/2009 | Silverbrook et al. | 73/729.2 |
| 7,586,106 | B2 * | 9/2009 | Kleinerman | 250/458.1 |
| 7,740,904 | B2 * | 6/2010 | Shahriari | 427/157 |
| 2006/0011820 | A1 | 1/2006 | Chow-Shing et al. | |
| 2008/0194933 | A1 * | 8/2008 | Kunze | 600/339 |
| 2008/0199360 | A1 * | 8/2008 | Shahriari | 422/82.06 |
| 2009/0028756 | A1 * | 1/2009 | Shahriari | 422/83 |
| 2010/0061678 | A1 * | 3/2010 | Swinehart et al. | 385/12 |

FOREIGN PATENT DOCUMENTS

| | | |
|---|---|---|
| WO | 03046422 A1 | 6/2003 |
| WO | 2012054913 A2 | 4/2012 |

OTHER PUBLICATIONS

Salour M M et al: "Semiconductor-Platelet Fibre-Optic Temperature Sensor", Electronics Letters, vol. 21, No. 4, Feb. 14, 1985, pp. 135-136, XP001412931.

Guangwei Liu et al: "Temperature and Pressure Detection System of Gas Tanks Using Fiber Bragg Grating", Control, Automation and Systems Engineering (CASE), 2011 International Conference on, IEEE, Jul. 30, 2011, pp. 1-3, XPO32046599, DOI: 10.1109/ICCASE.2011.5997877 ISBN: 978-1-4577-0859-6.

Lo Y L et al: "Temperature compensation of fluorescence intensity-based fiber-optic oxygen sensors using modified Stern-Volmer model", Sensors and Actuators B: Chemical: International Journal Devoted to Research and Development of Physical and Chemical Transducers, Elsevier S.A, CH, vol. 131, No. 2, May 14, 2008, pp. 479-488, XP-22635079, ISSN: 0925-4005, DOI: 10.1016/J. SNB.2007.12.010.

International Search Report for PCT/US2014/027057 dated Jul. 23, 2014.

* cited by examiner

OPTICAL PROBE CONTAINING OXYGEN, TEMPERATURE, AND PRESSURE SENSORS AND MONITORING AND CONTROL SYSTEMS CONTAINING THE SAME

This application is a continuation-in-part of, and claims benefit of the filing date of, U.S. application Ser. No. 13/279,994, filed Oct. 24, 2011, which claims benefit of U.S. Provisional Application No. 61/406,050, filed Oct. 22, 2010, the entire contents of which is incorporated herein by reference.

BACKGROUND

1. Field

Disclosed herein is an optical probe containing integrated oxygen, temperature, and pressure sensors. The probe is particularly suitable for determining the concentration of oxygen, particularly the partial pressure of oxygen, in an enclosed space, such as a fuel tank, cargo hold, passenger compartment, or other space in a vehicle, such as an aircraft, ship, boat, land vehicle, or other military, commercial, or aerospace vessel.

2. Description of Related Art

Since 1959, a number of aircraft fuel tanks have unexpectedly exploded. Typically, the explosions occurred when an unknown ignition source ignited the fuel/vapor mixture in the fuel tank. Fuel/vapor mixtures are created during consumption of fuel within the fuel tank by engines of the aircraft. The consumed fuel leaves a space within the tank which generally fills with atmospheric air containing oxygen. The presence of both a flammable gas and the fuel/vapor mixture within the space creates the potential for an explosion within the fuel tank upon ignition. The industry has responded with various methods and apparatuses, as discussed in Air Safety Week, Vol. 15 No. 16, Apr. 16, 2001, "Fatal Explosion Highlights Hazard of Flammable Vapors in Fuel Tanks." In addition, recent combat experience with fixed wing and rotary aircraft suggests that fuel tanks are susceptible to penetration by hostile fire, and in particular by shrapnel and small arms fire, which creates both an ingress for oxygen and a potential ignition source. Moreover, if lightning penetrates the wing or fuel tank of an aircraft as the result of a lightning strike, it can be a significant source of ignition, particularly in aircraft constructed using composite materials.

One method which reduces fuel/vapor combustion includes the elimination of combustible gases from the fuel tank. This method fills space within a fuel tank with an inert gas. The presence of the inert gas within the fuel tank deprives the fuel/vapor mixture of a flammable gas necessary for combustion. Nonetheless, the need to continuously fill the fuel tank with an inert gas and the attendant high costs associated therewith do not make this an attractive alternative for aircraft manufacturers.

A more efficient method in accordance with the prior art includes flooding the tank with inert gas when oxygen levels become high. This method requires continually measuring oxygen levels in a fuel tank. However, in order to accurately determine the oxygen concentration, either the temperature level of the oxygen sensor must be kept constant, or the temperature of the sensor must be measured in real time and taken into account in calculating the oxygen partial pressure from the sensor signal. Similar concerns arise with regard to the pressure in the vicinity of the oxygen sensor. However, temperatures and pressures within an enclosed space, such as fuel tanks in vehicles, can fluctuate over time depending on the outside temperature. In addition, spatial fluctuations in temperature and pressure within the fuel tank can occur. Moreover, these fluctuations can impact the ability of the monitoring and control electronics to accurately determine the oxygen level from the data obtained from the oxygen sensor.

Prior art attempts to address similar issues involved keeping the temperature of a gas sensor constant include heating the gas sensor with electric resistance heaters when the temperature is low. However, these methods are not suitable for use in fuel tanks, as electrical current applied to the electrical resistance heaters may potentially ignite the fuel/vapor mixture within the tank, again making this an unattractive option for aircraft manufacturers. Other attempts to provide fuel tank inerting systems and sensors include those described in U.S. Pat. Nos. 6,634,598; 6,904,930; 6,925,852; and 7,231,809. An oxygen probe containing a temperature sensor has also been developed, but the absence of an integrated pressure sensor requires that the system use pressure information from the aircraft pitot tubes. Such a system provides pressure information that is representative of the pressure in the fuel tank, but is based on the pressure outside of the aircraft. Alternatively, a pressure sensor system built into the fuel tank at a fixed position can provide erroneous information when the aircraft is not level. As a result, the pressure measurement from such systems is not accurate information about the ullage pressure in the vicinity of the probe, where the oxygen level is actually being measured.

Therefore, a need exists for a method and apparatus which provides accurate information about the temperature and pressure environment in the vicinity of the oxygen sensor, and that does not require potential sources of ignition, particularly in a vehicle fuel tank.

In addition, some vehicles, such as commercial and military aircraft, contain areas, such as cargo holds, passenger compartments, and the like, that may, expectedly or unexpectedly, contain materials capable of supporting combustion. Such areas can be equipped with fire suppression systems, which often are manually operated from the flight deck when an indication of a fire is received, generally from an increase in temperature in the cargo hold. However, there is typically no access to the cargo hold from the flight deck, and even if the fire suppression system is effective, temperature in the cargo hold may remain elevated for a considerable period of time. As a result, with such a system there is limited ability of the flight crew to determine in the short term whether the fire suppression system has been successfully deployed and has been effective in controlling the fire. Accordingly, there remains a need for a monitoring system that can allow a more rapid and accurate determination of whether fire suppression and control systems have been effective.

Fire suppression in passenger compartments provides a particular challenge, requiring precise control of the type and amount of fire suppression gas introduced, so as to decrease oxygen available for combustion while maintaining sufficient oxygen for life support of the passengers. Accurate monitoring of oxygen concentration in such a space is essential.

One technique that might be suggested as suitable for fuel tank inerting or monitoring is the On Board Inert Gas Generating System (OBIGGS system). This system processes pressurized air through hollow fiber membranes to obtain a nitrogen enriched air, which can be used as an inerting gas. However, the implementation of this system is not optimal, because of the lack of an appropriate sensing/control system. As a result, attempts have been made to operate OBIGGS equipped aircraft with the system constantly operational (i.e., continuously supplying nitrogen to the ullage of the aircraft fuel tanks). Such an operation, however, incurs a significant fuel penalty. Accordingly, there remains a need in the art for a sensing/control system that allows an inerting system such as OBIGGS to be operated when necessary (i.e., when the oxygen partial pressure in the ullage of the fuel tank reaches a predetermined value) and to be idled when operation is not necessary, thereby increasing fuel economy. Such an idled mode includes heating of the system to prevent freezing of moisture in the system.

Accordingly, there remains a need in the art for a probe that provides accurate, localized information about oxygen concentration, pressure, and temperature, and that is capable of operating under the stringent environmental conditions found in, e.g., an aviation fuel tank. These conditions include operation under widely varying temperatures, operation under low temperatures, operation while exposed to the components of fuels, and particularly while exposed to the hydrocarbons in various aviation fuels, such as jet fuels, and operation under vibration.

SUMMARY

In one embodiment is disclosed a probe for measuring oxygen, temperature, and pressure in a space to be monitored, comprising:
  a housing, comprising a thermally conductive material;
  an oxygen sensor disposed within the housing, comprising:
    a first end having coated thereon a coating which fluoresces at a fluorescent frequency when exposed to light having an excitation frequency in the absence of associated oxygen, and which undergoes a dampening of said fluorescence in the presence of associated oxygen; and
    a second end operatively connected to an optical fiber that extends through the housing;
  wherein the first end extends through the housing and is adapted to be exposed to the space to be monitored;
  a temperature sensor disposed within the housing adjacent to the thermally conductive material, wherein the temperature sensor does not extend through the housing and is not exposed to the space to be monitored;
  a pressure sensor disposed within the housing, having a first end which extends through the housing and is adapted to be exposed to the space to be monitored.

Desirably, the temperature sensor may include a fiber Bragg grating or a semiconductor crystal, such as a gallium arsenide crystal. Desirably, the pressure sensor may include a fiber Bragg grating or a Fabry-Pérot white light interferometry sensor. The temperature sensor and pressure sensor may be integrated into a single sensor disposed within the probe tip.

In another embodiment is disclosed a system for monitoring the level of oxygen in a space to be monitored, comprising:
  the probe described herein; and
  an analyzer for calculating oxygen partial pressure based upon the fluorescence damping, temperature, and pressure data provided by the probe.

In another embodiment is disclosed a system for controlling the concentration of oxygen in a space, comprising:
  the system for monitoring the level of oxygen in the space, as described herein; and
  a controller for introducing an inert gas into the space when the level of oxygen in the space reaches a predetermined level.

In another embodiment is disclosed a vehicle comprising the system for controlling the concentration of oxygen in a space as disclosed herein.

In another embodiment is disclosed a method for monitoring the level of oxygen in a space equipped with a probe as described herein, comprising:
  obtaining fluorescence damping data from the oxygen sensor;
  obtaining temperature data from the relative Bragg wavelength shift of the temperature sensor;
  obtaining pressure data from relative Bragg wavelength shift of the pressure sensor taking into account the temperature data from the temperature sensor;
  determining the partial pressure of oxygen from said fluorescence damping data, said temperature data, and said pressure data.

In another embodiment is disclosed herein a method for controlling the level of oxygen in a space, comprising:
  monitoring the level of oxygen in the space as disclosed herein;
  controlling the introduction of an inert gas into the space by introducing said inert gas into the space when the level of oxygen reaches a predetermined level.

Because each of the sensors is located at the probe tip, data on oxygen concentration, temperature, and pressure are obtained at that location, providing a more accurate, real time, in situ determination and calculation of oxygen concentration, and therefore better monitoring and control of the level of oxygen in the space being monitored. Moreover, because no sample removal is required and data acquisition occurs within the space being monitored, accuracy is also increased. For example, embodiments of the probe and system described herein provide a sensor dynamic range of oxygen concentration ranging from 0% (total inertness) to 25% (in excess of air), with a resolution of 0.1% and an accuracy of 0.5% $O_2$, and a sensor response time of a few seconds.

The use of fiber optics, rather than electronics, to gather and transmit data decreases the risk of an unanticipated ignition source as compared to electronic systems, because it is not the source of electrical or electrostatic sparks, does not produce a current, and is not otherwise an ignition source. Moreover, the probe and systems described herein is not affected chemically, physically, or functionally by exposure to liquid or vaporized fuel, which decreases the risk of adverse affects by contact with hydrocarbons (e.g. adverse interactions between aircraft fuel and galvanic cell membranes), and eliminates the need for heating resulting from the use of zirconium electrochemical cells, as well as eliminates any consumption of oxygen to operate the system. Moreover, the systems described herein are expected to require less frequent calibration, and to be less susceptible to interferences (such as EMI interference) than existing technologies. Embodiments of the probe described herein can be multiplexed to a single control unit, allowing multiple locations in a space to be monitored simultaneously.

Embodiments of the probe described herein are resistant to hydrocarbon exposure, resistant to the effects of thermal shock and pressure changes experience, e.g., during flight. For example, embodiments of the probe and system described herein can operate over a temperature range of −50 to +80° C., and over a pressure range of ambient to +2 psi. The probe described herein allows the vehicle operator to confirm that inerting or fire suppression is occurring as needed and according to specifications, to determine the inertness of the space being monitored, and allows for a closed loop control of oxygen levels in the space being monitored. Moreover, the system is small, light weight, and compatible with automatic control systems onboard the vehicle.

BRIEF DESCRIPTION OF DRAWINGS

Illustrative embodiments disclosed herein can be more clearly understood by reference to the following drawings, wherein the same reference numerals indicate the same structure.

DETAILED DESCRIPTION OF SPECIFIC EMBODIMENTS

As used herein, the term "about" in connection with a numerical value or range of numerical values denotes somewhat above and somewhat below the stated numerical value, to a maximum deviation of ±10%.

Figure 1:
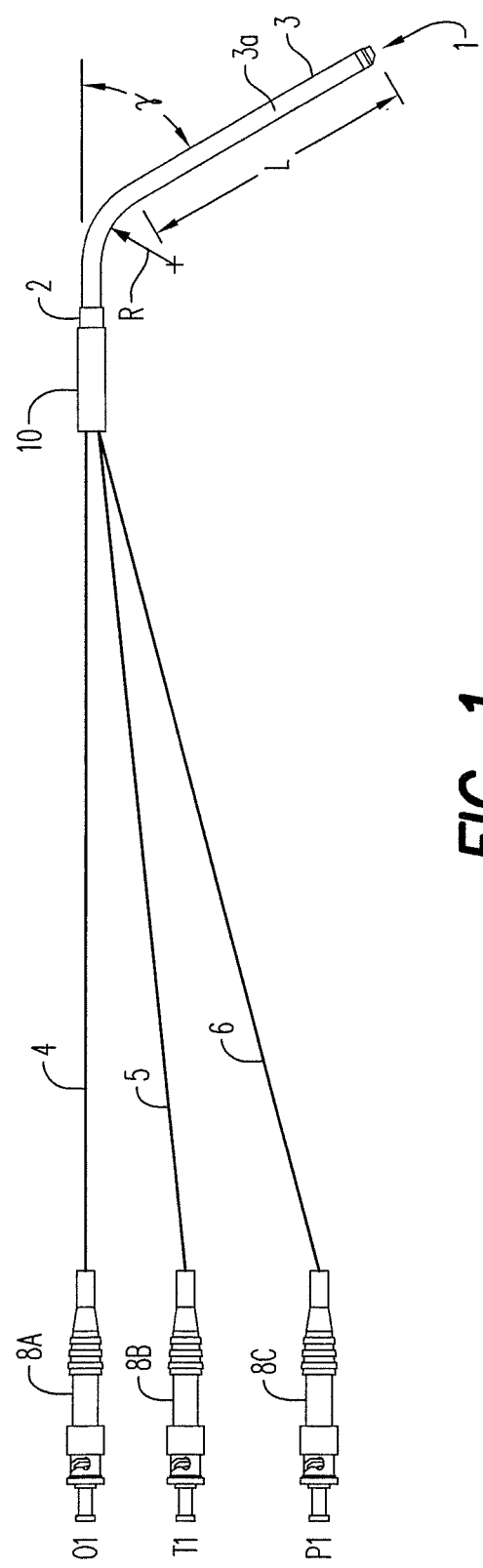
FIG. 1 is a schematic view of an integrated oxygen probe having oxygen, temperature, and pressure sensors according to an embodiment disclosed herein.

A particular embodiment of an integrated oxygen, temperature, and pressure probe is shown schematically in FIG. 1. Probe tip 1 is disposed at one end of probe tube 3. At the other end of probe tube 3 is disposed probe cover 2, adjacent to heat shrink tube 10. The probe tip 1 contains an oxygen sensor, a temperature sensor, and a pressure sensor, all connected to optical fibers (4, 5, and 6) (e.g., 1000-1100 micron fiber is generally suitable, however other fiber sizes can be used) enclosed within a polymeric tube (e.g., PTFE tube). In the illustrated embodiment, each optical fiber is connected to an optical connector (8A, 8B, and 8C) suitable for connection to an optoelectronic monitoring and/or control system (not shown). FIG. 1 provides representative dimensions with respect to distances, radii of curvature, and angular measurements for a particular exemplary embodiment, and may be varied substantially as specific circumstances require or permit. For example, R, representing a radius of curvature of the probe, may generally be greater than or equal to 0, more particularly greater than or equal to 1.3 inches, and is dependent to some degree on the properties and thickness of the optical fibers used in the probe. In some applications, no curvature in the probe will be necessary or desirable, so that there will be no radius of curvature. Similarly, angle γ will also depend upon the thickness and properties of the fiber, and may range from 0° to 75°, more particularly from 0° to 60°, even more particularly from 0° to 45°. The length L can also be substantially variable, but is generally greater than or equal to 3 inches, more particularly greater than or equal to 5 inches. Factors that may influence the various dimensions and geometry of the system include the particular platform in which the system is installed, the particular mounting used, clearances in the vicinity of the mounting, etc.

Figure 2:
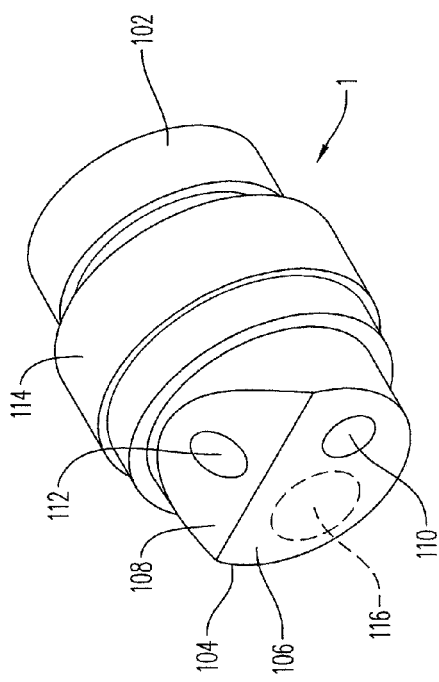
FIG. 2 is a perspective view of an embodiment of an oxygen probe tip suitable for use in the oxygen sensor of FIG. 1

FIG. 2 is a perspective view of an embodiment of probe tip 1, showing distal end 102, which is adapted to connect to one end of probe tube 3, and proximal end 104, which is exposed to the environment of the space to be monitored. In the embodiment shown, proximal end 104 contains a flat portion 106 and a beveled portion 108, although this geometry is exemplary and other geometries are possible. Flat portion 106 contains pressure sensor 110 and temperature sensor 116 (shown as a dotted line in FIG. 2). The proximal end of pressure sensor 110 is, in this embodiment, exposed to the environment of the space to be monitored, while temperature sensor 116 is separated from the environment of the space to be monitored by a thin layer of thermally conductive material, desirably the metal forming the flat portion 106 of the probe tip 1. Beveled portion 108 contains oxygen sensor 112, the proximal end of which is also exposed to the environment of the space to be monitored. Between proximal end 104 and distal end 102 is probe tip body 114, which, like distal end 102 is desirably hollow, allowing sufficient space for the fibers connected to pressure sensor 110, temperature sensor 116 and oxygen sensor 112 to pass through the probe tip 1 to the probe tube 3, and to provide sufficient rigidity. The probe tube 3 can desirably be filled with vibration dampening material, such as silicone, indicated by 3a in FIG. 1, to restrict fiber movement and/or dampen vibrations experienced by the system during operation.

Figure 3B:
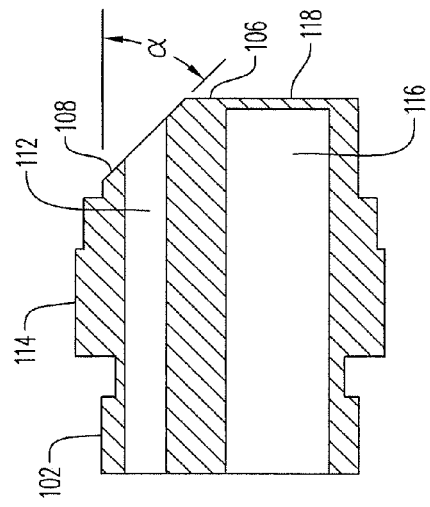
FIG. 3B is a sectional view along section line A-A of FIG. 3A.
Figure 3A:
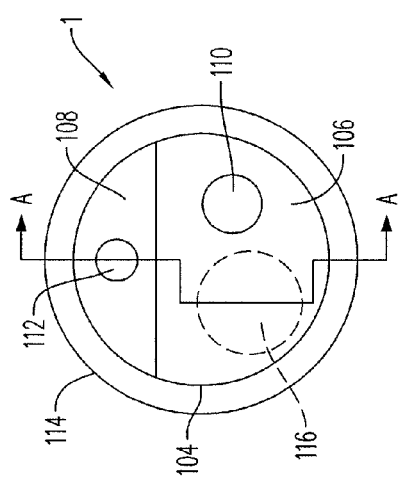
FIG. 3A is a front plan view of the oxygen probe tip of FIG. 2.

FIG. 3A is a front plan view of proximal end 104 of probe tip 1, showing the arrangement of flat portion 106 and beveled portion 108, as well as the arrangement of pressure sensor 110, temperature sensor 116 (shown in dotted line) and oxygen sensor 112. FIG. 3B is a sectional view along section line A-A in FIG. 3A. Temperature sensor 116 is visible in this view, and is separated from the environment to be monitored by a thin piece of thermally conductive material 118. The angle of bevel a can be substantially variable, but generally ranges from about 30° to about 60°, more particularly about 45°.

Figure 4:
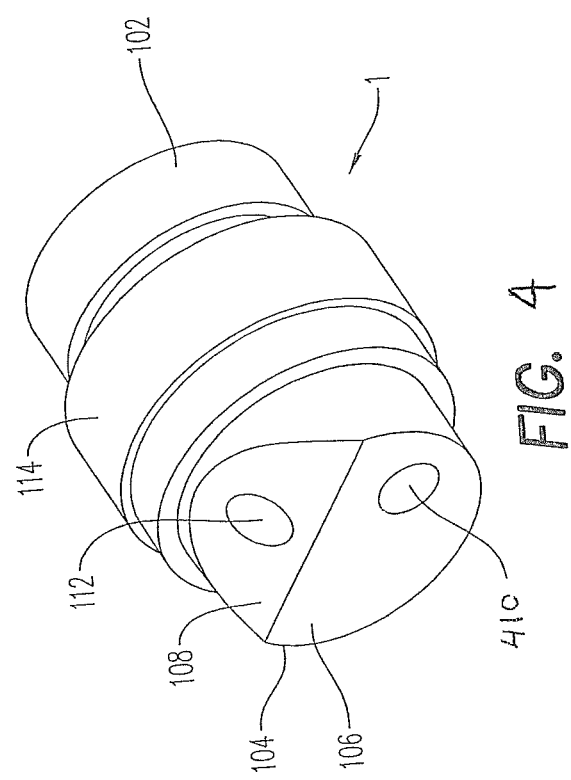
FIG. 4 is a perspective view of another embodiment of an oxygen probe tip, wherein the temperature sensor and pressure sensor have been integrated together within the probe tip.

FIG. 4 is a perspective view of another embodiment of a probe tip where the temperature sensor has been integrated with the pressure sensor within the probe tip, the integrated pressure/temperature sensor being indicated by reference numeral 410. Such integrated pressure and temperature sensors are available from FISO Technologies Inc., Quebec, Canada, and may take the form of a gallium arsenide temperature sensor, disposed behind a Fabry-Pérot white light interferometry sensor for measuring pressure. The pressure sensor is exposed to conditions in the space to be measured, while the temperature sensor, which is immediately behind the pressure sensor, is not. Each sensor retains its own optical fiber for transmission of information. The gallium arsenide material senses temperature as the result of the variance in white light absorption and transmission with varying temperature. The Fabry-Pérot white light interferometry sensor or piezometer functions as described in Pinet, Fabry-Pérot Fiber-Optic Sensors for Physical Parameters Measurement in Challenging Conditions, Journal of Sensors, 2009, 720980, incorporated herein by reference. For such a pressure sensor, a reflecting deformable membrane is assembled over a generally vacuumed cavity made in a transparent material, thus forming a small drum. The bottom of the cavity and the inner flat surface of the flexible membrane are forming the sensing Fabry-Pérot cavity. When pressure is applied, the membrane deflects, thus changing the Fabry-Pérot cavity length. With appropriate sensor calibration, each cavity length corresponds to a pressure value that is displayed.

Figure 5:
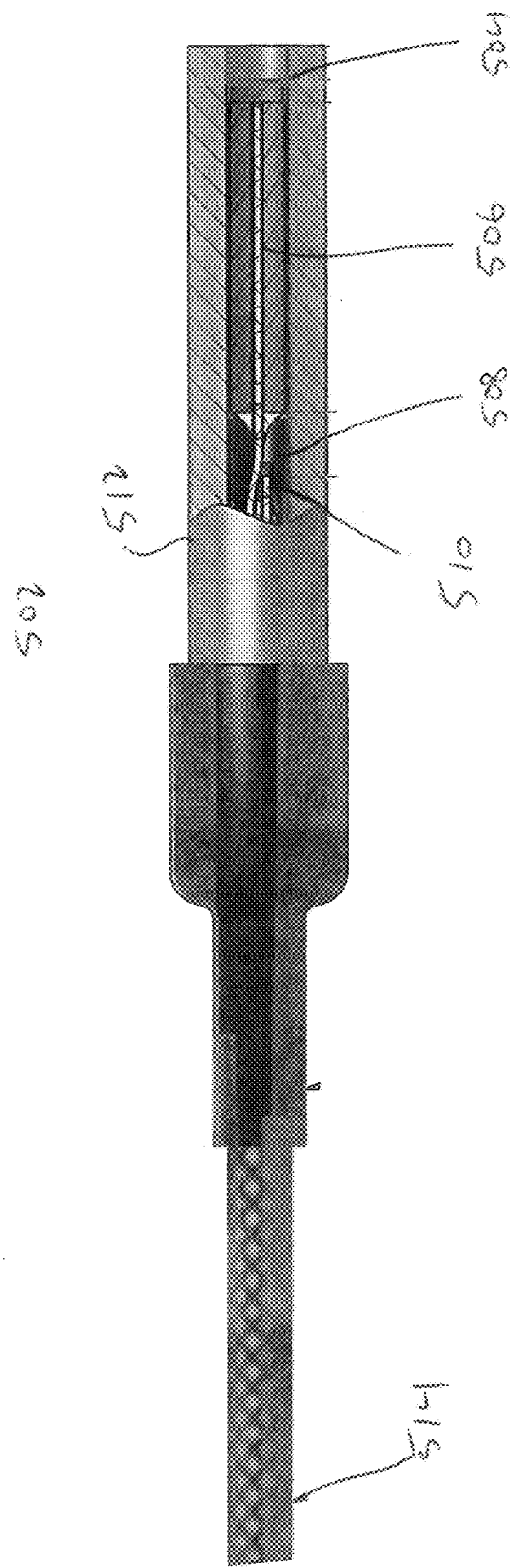
FIG. 5 is a partial cutaway view of an embodiment of an integrated temperature/pressure sensor.

FIG. 5 is a partial cutaway view of an embodiment of an integrated pressure/temperature sensor 502 suitable for use in the probe tip disclosed herein. Within a housing 512 are disposed pressure sensor 504, which may be a Fabry-Pérot white light interferometry sensor or piezometer, and which is connected to an optical fiber 506. Disposed within the housing 512 operatively behind pressure sensor 504 is a temperature sensor 508, which is connected to another optical fiber 510. Temperature sensor 508 may be another Fabry-Pérot white light interferometry sensor or may be a gallium arsenide material. Optical fibers 506 and 510 can be combined to form optical cable 514, or can be maintained as separate optical fibers, which can be connected to the desired processing electronics.

The oxygen sensor may desirably be of the fluorescence damping type described in U.S. Pat. Nos. 6,634,598; 6,904, 930; 6,925,852; 7,231,809, 7,740,904, and in U.S. Patent Application Publication Nos. 2008/0199360 and 2009/0028756, the entire contents of each of which are incorporated herein by reference.

The temperature sensor may be of a fiber Bragg type, wherein the Bragg wavelength is sensitive to temperature. Without wishing to be bound by theory, it is believed that a change in temperature in the space being monitored results in a shift in the Bragg wavelength $\Delta\lambda_B/\lambda_B$, according to a relationship of the form:

$$\left[\frac{\Delta\lambda_B}{\lambda_B}\right] = C_S \varepsilon + C_T \Delta T$$

wherein $\varepsilon$ is an applied strain, $C_S$ is the coefficient of strain, $C_T$ is the coefficient of temperature, and $\Delta T$ is the temperature difference. By maintaining the temperature sensor behind a layer of thermally conductive material, the contribution of strain to the shift in Bragg wavelength is reduced or eliminated, and the shift is thus the result of the change in temperature in the space to be monitored, at least a portion of which is seen by the fiber Bragg sensor through the thermal conduction of the layer of thermally conductive material.

The pressure sensor may also be of a fiber Bragg type, wherein the tip of the fiber Bragg grating is directly exposed to the space to be monitored. Without wishing to be bound by theory, it is believed that the resulting shift in Bragg wavelength will be the result of the contribution of the strain experienced by the pressure sensor as the result of the change in pressure, and of the contribution from the change in temperature. Since the temperature contribution is known from the temperature sensor, the strain contribution can be determined via a suitable algorithm, and the resulting pressure change determined.

Suitable fiber Bragg grating transceiver systems suitable for use with the fiber Bragg grating temperature and pressure sensors described above include those available from Redondo Optics, Inc. (FBG-Transceiver™). Pressure, temperature, and oxygen level data obtained from the probe described above may be sent to an analysis system, such as a multi-channel interrogation system. One example of a suitable system is the FOxSense™ multichannel interrogation system available from Redondo Optics, Inc. The data is analyzed using a suitable algorithm, such as one using the Stern-Volmer relationship, to determine the partial pressure of oxygen in the space being monitored, such as the ullage of a fuel tank, cargo hold, passenger compartment, etc. This information can, in turn, be used to control and monitor an inerting system of the type described in U.S. Pat. Nos. 6,634,598; 6,904,930; 6,925,852; and 7,231,809, an OBIGGS system, a halon fire suppression system, a nitrogen/water mist passenger compartment fire suppression system, and the like, on an aircraft, waterborne vessel, tank or armored vehicle, etc.

Alternatively, as described above, the pressure and/or temperature sensors may be of the Fabry-Pérot white light interferometry type. Alternatively, the temperature sensor may be a gallium arsenide sensor, or may be formed of another material having temperature sensitive light absorption and/or transmission characteristics.

Desirably, if the probe and the monitoring and control systems described herein are operated to provide inerting of, e.g., a vehicle fuel tank, the oxygen concentration therein is maintained at a level below about 9% by volume (for military aircraft) and below about 11-12% by volume (for commercial aircraft) at atmospheric pressure.

What is claimed is:

1. A probe for measuring oxygen, temperature, and pressure in a space to be monitored, comprising:
    a housing, comprising a thermally conductive material;
    an oxygen sensor disposed within the housing, comprising:
        a first end having coated thereon a coating which fluoresces at a fluorescent frequency when exposed to light having an excitation frequency in the absence of associated oxygen, and which undergoes a dampening of said fluorescence in the presence of associated oxygen; and
        a second end operatively connected to an optical fiber that extends through the housing;
        wherein the first end extends through the housing and is adapted to be exposed to the space to be monitored;
    a temperature sensor disposed within the housing adjacent to the thermally conductive material, wherein the temperature sensor does not extend through the housing and is not exposed to the space to be monitored;
    a pressure sensor disposed within the housing, having a first end which extends through the housing and is adapted to be exposed to the space to be monitored.

2. The probe according to claim 1, wherein the temperature sensor or the pressure sensor, or both, comprise a fiber Bragg grating.

3. The probe according to claim 1, wherein the temperature sensor comprises a semiconductor material.

4. The probe according to claim 1, wherein the temperature sensor comprises a gallium arsenide material.

5. The probe according to claim 1, wherein the pressure sensor comprises a Fabry-Pérot white light interferometry sensor.

6. The probe according to claim 1, wherein the temperature sensor comprises a gallium arsenide material and the pressure sensor comprises a Fabry-Pérot white light interferometry sensor.

7. The probe according to claim 1, wherein the temperature sensor and the pressure sensor are integrated together within the probe tip.

8. A system for monitoring the level of oxygen in a space to be monitored, comprising:
    the probe according to claim 1; and
    an analyzer for calculating oxygen partial pressure based upon the fluorescence damping, temperature, and pressure data provided by the probe.

9. A system for controlling the concentration of oxygen in a space, comprising:
    the system for monitoring the level of oxygen in the space, according to claim 8; and
    a controller for introducing an inert gas into the space when the level of oxygen in the space reaches a predetermined level.

10. A vehicle comprising the system for controlling the concentration of oxygen in a space according to claim 9.

11. A method for monitoring the level of oxygen in a space equipped with a probe according to claim 1, comprising:
    obtaining fluorescence damping data from the oxygen sensor;
    obtaining temperature data from the temperature sensor;
    obtaining pressure data from the pressure sensor taking into account the temperature data from the temperature sensor;
    determining the partial pressure of oxygen from said fluorescence damping data, said temperature data, and said pressure data.

12. A method for controlling the level of oxygen in a space, comprising:

monitoring the level of oxygen in the space according to claim 11;
controlling the introduction of an inert gas into the space by introducing said inert gas into the space when the level of oxygen reaches a predetermined level.

* * * * *